United States Patent [19]

Yip

[11] Patent Number: 5,464,777
[45] Date of Patent: * Nov. 7, 1995

[54] DRY REAGENT FOR CREATININE ASSAY

[75] Inventor: Kin-Fai Yip, Elkhart, Ind.

[73] Assignee: Miles Inc., Elkhart, Ind.

[*] Notice: The portion of the term of this patent subsequent to Jan. 31, 2012, has been disclaimed.

[21] Appl. No.: 312,559

[22] Filed: Sep. 26, 1994

[51] Int. Cl.⁶ ............... G01N 33/546; G01N 33/53; G01N 33/557

[52] U.S. Cl. ............... 436/98; 436/534; 436/518; 435/7.1; 435/973

[58] Field of Search ............... 436/98, 106, 909, 436/534, 518; 435/7.1, 973, 962

[56] References Cited

U.S. PATENT DOCUMENTS 5,385,847  1/1995  Yip ............... 436/534

FOREIGN PATENT DOCUMENTS 1578234  8/1969  France .
1266     8/1984  WIPO .

OTHER PUBLICATIONS

Benedict et al, J. Biol. Chem., vol. 114, 1936.

Primary Examiner—James C. Housel
Assistant Examiner—Michael L. McGlashen
Attorney, Agent, or Firm—Jerome L. Jeffers

[57] ABSTRACT

A method for the determination of protein and creatinine in urine. An organic acid, in the form of its lithium salt, is dried onto a suitable substrate in the second reaction zone of a reaction vessel having a first reaction zone for the immunometric determination of the protein and a second reaction zone for the colorimetric determination of creatinine. After completion of the immunometric determination of the protein the dried organic salt is contacted with the urine containing creatinine resulting in solubilization of the organic acid salt as creatinine reactive reagent thereby facilitating the colorimetric determination of the creatinine.

6 Claims, 3 Drawing Sheets

DRY REAGENT FOR CREATININE ASSAY

BACKGROUND OF THE INVENTION

Creatinine is the end metabolite when creatine becomes creatine phosphate and is used as the energy source for muscle contraction. This creatinine is filtered by the kidney glomeruli and then excreted into the urine without reabsorption. The determination of creatinine in body fluids is useful for diagnosing muscle diseases or various kidney diseases such as nephritis and renal insufficiency.

The first practical test for the determination of creatinine in urine, known as the Jaffe method, involves the formation of the red-yellowish brown colored creatinine picrate by the bonding of picric acid and creatinine in an alkaline solution. A more recent method for creatinine determination is reported by Benedict and Behre *J. Biol. Chem.*, 113:515 (1936) which involves the reaction of 3,5-dinitrobenzoic acid with creatinine in an alkaline medium. The colorimetric determination of creatinine requires a high pH, on the order of from about 11.5 to 12.5, in order to deprotenate the creatinine enabling it to form the colored reaction product. Strongly basic substances such as alkali and alkaline earth metal hydroxides are typically used to maintain a suitably high pH in the reagent systems.

In jointly assigned U.S. Pat. No. 5,385,847 there is disclosed a unitary method for the determination of urinary protein and creatinine in a single urine sample. In this sort of assay the creatinine determination is used to minimize the problem of high urine flow by using the protein/creatinine ratio to normalize the urine concentration. There is described in this disclosure a method for the unitary determination of urinary protein and creatinine in which a urine sample is introduced into a reaction vessel containing first and second reaction zones. The first reaction zone is incorporated with a dry immunoreagent specific for the urinary protein and the second reaction zone is incorporated with a dry basic reagent capable of raising the pH of a reaction fluid introduced into the reaction zones to a level suitable for creatinine determination. When the urine sample is introduced into the first reaction zone and brought into contact with the immunoreagent and a reaction fluid containing a polymeric agglutinator, it dissolves the immunoreagent causing an increase in the turbidity of the reaction fluid due to the interaction of the immunoreagent and the urinary protein which increase in turbidity can be used to determine the concentration of the urinary protein. Next, the reaction fluid, which contains a reagent for the determination of creatinine is brought into contact with the dry basic reagent in the second reaction zone to thereby dissolve the basic reagent and raise the pH of the reaction fluid to a level necessary for the colorimetric determination of creatinine. Alternatively, the creatinine determining reagent is pre-dried onto the surface of the second reaction zone along with the basic reagent. In order for this system of unitary analysis to operate at peak efficiency, it is essential that the dry creatinine reactive reagent be dried onto the surface of the second reaction zone in sufficient quantity to facilitate the creatinine determining reaction upon rehydration of this reagent.

The use of lithium salts in analytical procedures is known. For example in U.S. Pat. No. 5,151,369 there is disclosed a method of red blood cell lysing and hemoglobin denaturing in which lithium salts, particularly lithium thiocyanate, are used.

SUMMARY OF THE INVENTION

The present invention is an improvement to the assay for creatinine in aqueous solution in which an organic acid reagent which reacts with creatinine under alkaline conditions to form a colored reaction product is contacted with an aqueous solution containing creatinine and is solubilized by said solution. The improvement comprises the use of the lithium salt of the creatinine reactive reagent.

DESCRIPTION OF THE INVENTION

Figure 1:
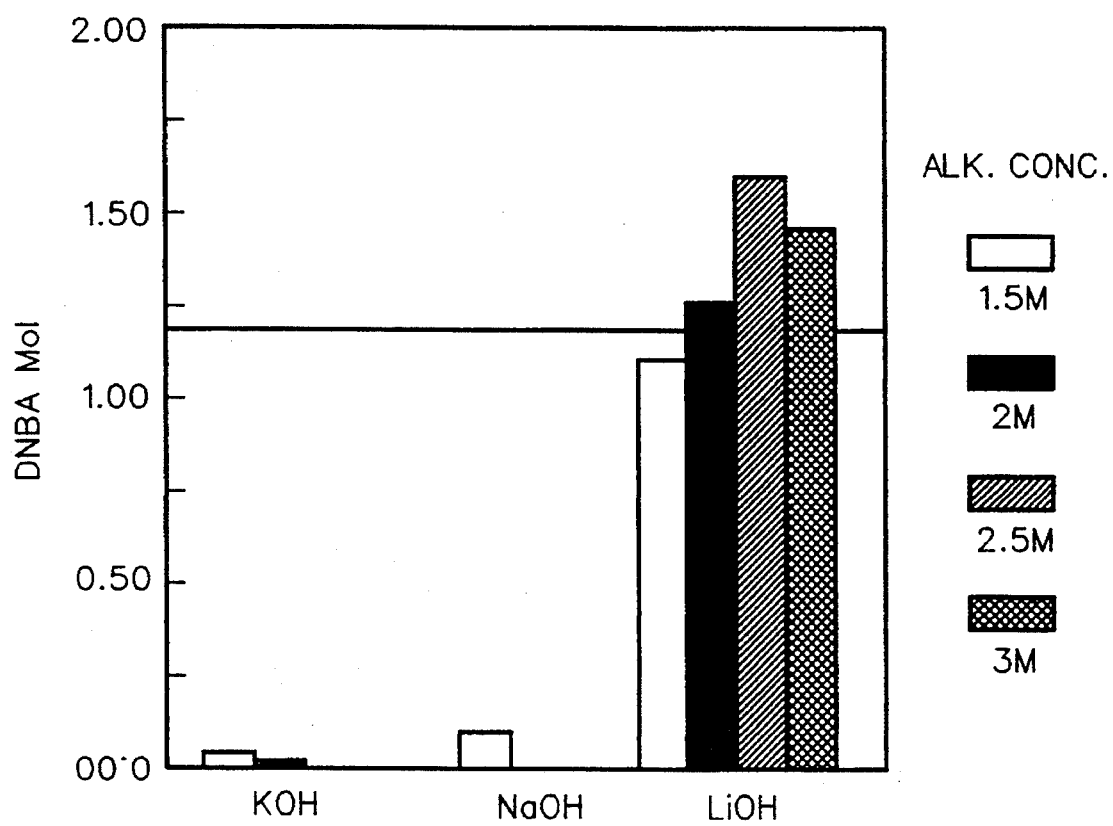
FIG. 1 is a graphical representation of an experiment in which the solubilities of potassium, sodium and lithium dinitrobenzoic acid were compared.

The use of the lithium salt of an organic acid as creatinine detecting reagent, such as Lithium dinitrobenzoic acid (LiDNBA), lithium picrate and lithium 1,4-naphthoquinone-2-sulfonate is useful in any sort of analytical scheme in which such a dried reagent is used. For example, the lithium salt can be used in a dry reagent strip format in which a dip solution of the salt, e.g. LiDNBA, and LiOH (or other base) is used to impregnate the strip matrix. Such a reagent strip will react with creatinine in the sample to generate a colored response. Alternatively, the strip can be prepared using a two dip format in which the first dip contains the lithium salt and the second dip contains an alkaline reagent in an alcohol/water mixture. Any analytical technique for the determination of creatinine in which a creatinine reactive reagent is dried onto a supporting material for later resolubilization by an aqueous fluid, such as urine, whose creatinine concentration is to be measured, can benefit from using the present invention. In the case of DNBA, the best known of the creatinine reagents, there is reported in the literature a solubility for the free acid of only about one gram in 53 parts of boiling water (0.089M) and considerably less solubility in cold water. One would expect that DNBA would be more soluble in the form of its salts. Experimental results indicated that the solubility of DNBA potassium salt at room temperature is about 0.05M, and the solubility of the sodium salt at room temperature is about 0.11M. Unexpectedly, it was discovered that the room temperature solubility of the lithium salt of DNBA is about 1.89M. Mixtures of DNBA salts also have moderate solubility; for example the mixture of its sodium and potassium salts exhibited a solubility of 0.58M, whereas the mixture of its sodium and lithium salts has a solubility of 0.92M and the mixture of potassium and lithium salts exhibits a solubility of 0.91M at room temperature. Because of its high solubility, the lithium salt is preferred for use in this sort of analysis where the creatine reagent is dried onto a solid support since the greater the concentration of the salt of the creatinine reactive substance, the greater the amount of salt that can be deposited from a given amount of the solution. Furthermore, when the DNBA or other creatinine reactive material is to be resolubilized, such resolubilization is facilitated by the use of the lithium salt.

As previously mentioned, the present invention is particularly useful in combination with the device for the unitary measurement of urinary protein and creatinine disclosed in U.S. Pat. No. 5,385,847. In this system, in which the urine to be tested is introduced into a reaction vessel containing first and second reaction zones, there can be incorporated in the first reaction zone, for example, dried goat antiserum against human serum albumin (HSA). This material is commercially available and can be used without additional treatment except that it is typically concentrated two-fold and combined with 2–5% of a sucrose/trehalose mixture to stabilize the antibody during drying and during its long term storage after having been dried. The additives also provide physical stability to prevent peeling and caking of the dried reagent. Typically a 15 µL portion of a solution of the antibody is dried onto the first reaction zone and dried using a drying tunnel operated at 60° C. for a 15 minute period.

The alkaline reagent and creatinine reactive reagent are dried onto the surface of the second reaction zone, typically on different surfaces thereof to keep them separated prior to their resolubilization. The alkaline reagent for creatinine determination consists either of an alkali hydroxide solution (e.g. 2.5M KOH) or a mixture of alkaline buffering material such as phosphate, borate or guanidine derivatives together with alkali hydroxide. Typically a mixture of 1M phosphate and 4.0M potassium hydroxide as well as 10% of the additive described above is used. This reagent is dried onto one surface of the second reaction zone by applying, for example, 15 µL of its concentrated solution to one surface of the second reaction chamber and dried. The creatinine reactive reagent, typically Li 3,5-dinitrobenzoate in water, is provided in a fairly saturated, e.g. 1.4M solution. Full saturation up to the solubility limit of the LiDNBA can be employed, but is not desirable during the manufacturing process because solid material can be generated easily from the saturated solution due to minor changes in concentration and temperature. This solution will normally be treated with a stabilizing additive of the type described above and applied to the appropriate surface of the second reaction zone from 15 µL of solution with subsequent drying.

In operation, a buffer, (e.g. 4% polyethylene glycol, 25 mM Tris, 5 mM EDTA, 0.1% sodium azide and 0.1% gelatin, pH=8.5) and 30 µL of sample which can consist of HSA, creatinine or a mixture of HSA and creatinine, is introduced into the device to initiate the reaction. After measurement of the blank, the antibody reagent is dissolved and the absorption at 531 nm is measured for 2 minutes. The rate of increase of the absorption is proportional to the concentration of the HSA in the sample. Next the alkaline reagent and the LiDNBA are dissolved and the absorption at 531 nm is again measured for three minutes with the rate of increase in the absorption being proportional to the concentration of the creatinine in the sample.

The present invention is further illustrated by the following examples:

EXAMPLE I

The solubility of DNBA in aqueous solutions of KOH, NaOH and LiOH was determined as follows:

Dinitrobenzoic acid was added to 1.5, 2.0, 2.5 or 3.0M solutions of potassium, sodium and lithium hydroxide until insoluble DNBA was observed. The resultant was stirred and allowed to stand at room temperature for one hour whereupon the DNBA saturated supernatants were removed and the concentration of the alkali metal salt in solution was determined by UV absorption at 340 nm.

The results of this experiment are graphically set out in FIG. 1 from which it can be determined that a five to ten fold more concentrated solution can be prepared from DNBA with lithium hydroxide than with the use of either potassium or sodium hydroxide.

EXAMPLE II

The combined analysis of urinary protein and creatinine works well in a wet analysis format and it has been found to be particularly suitable for adaptation to a reaction vessel for performing sequential analytical assays such as that disclosed in U.S. Pat. No. 4,990,075. This patent discloses a reaction vessel having a substantially horizontal axis of rotation and an analytical reagent reaction channel containing first and second reaction zones incorporated with first and second analytical reagents which interact with an analyte in a liquid test sample to produce a detectable response as a function of the analyte. The second reaction zone is situated a predetermined distance away from and in fluid communication with the first reaction zone whereby a liquid test sample disposed in the reaction channel is capable of being transported by gravity along the reaction channel between the reaction zones by rotating the reaction vessel about its axis of rotation. The reaction vessel has liquid test sample delivery means for providing a unidirectional flow of the liquid test sample into the reaction vessel and inlet means in liquid communication with the delivery means for introducing the liquid test sample into the delivery means.

Figure 2:
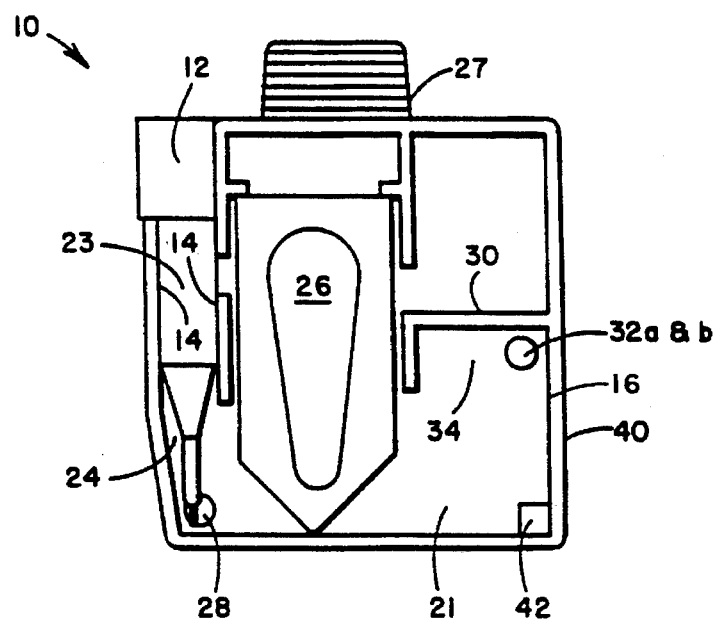
FIGS. 2–5 represent a device which can be used to determine concentrations of protein and creatinine in a single urine sample.

Referring to FIG. 2, a mixture of the antibody and an additive such as a monosaccharide, disaccharide or oligosaccharide is dried onto the first reaction site 28 in the first reaction chamber 24 of the reaction vessel 10. In addition to the previously mentioned attributes, the additives also provide physical stability to prevent peeling and cracking of the dried reagent. The device has inner walls 14 which form a delivery chamber 23 permitting the introduction of a liquid test sample, such as a small amount of urine, into the device, and, since the delivery chamber is in fluid communication with the reaction channel 21, the liquid test sample can enter the reaction channel through the delivery chamber and be caused to flow along the reaction channel by clockwise rotation of the device along its horizontal axis of rotation. The test sample is conveniently delivered through capillary dispenser 12 as inlet and delivery means as depicted in FIG. 2. Since only a small amount of urine will be introduced through the delivery channel, additional reaction fluid containing suitable buffers can be introduced either through the delivery channel or from another source such as liquid delivery reservoir 26 adapted to contain a buffer and/or liquid reagent for performing the analytical assay procedures of the present invention. Typically, the reaction fluid will contain a polymeric agglutinator which specifically binds with an antibody reagent located in the first reaction zone to provide an agglutination type immunoassay. The liquid delivery reservoir comprises a reservoir body 27 having a depression therein 26 to act as a fluid reservoir for holding the fluid until needed and is covered by a membrane (not shown) which can be removed to allow the fluid in the reservoir 26 to flow into reaction channel 21. Simple manipulation of the device will cause the test sample carried by the fluid from fluid reservoir 26 to flow into position for viewing through viewing chamber 42.

Figure 3:
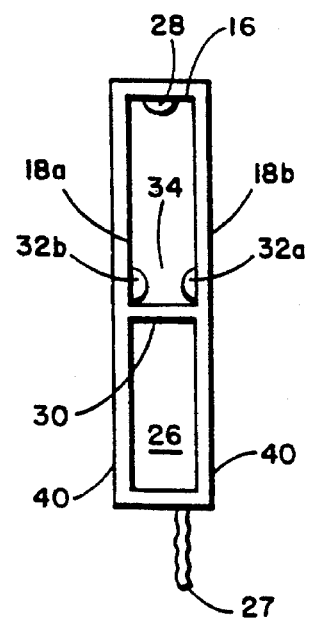
Figure 4:
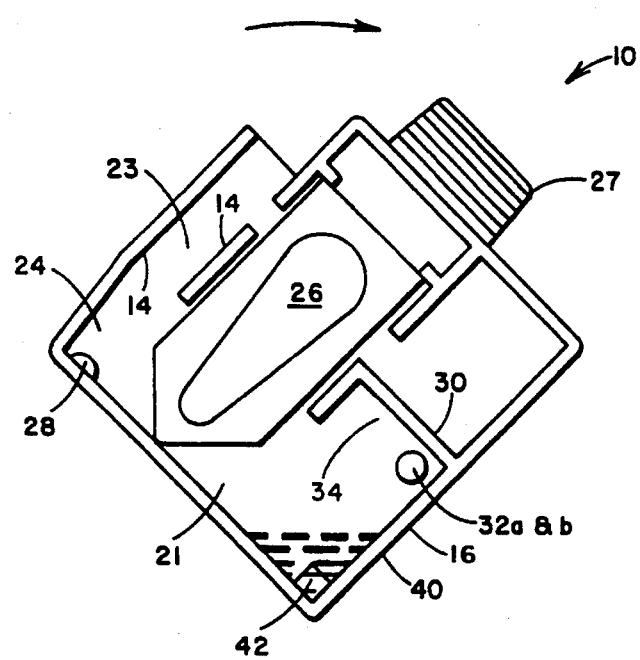

The first reaction zone contains dried antibody reagent at the first reaction site 28 which is typically attached to one of the side walls depicted as 18a and 18b in FIG. 3 or to the inner wall 16 of the reaction vessel. Suitable rotation of the device will bring the reaction fluid into contact with the dried antibody reagent at site 28 to facilitate its dissolution so that it can react with the agglutinator in the agglutination immunoassay. When the antibody reagent is adequately dissolved in the reaction fluid carrying the urine test sample, the device 10 is rotated 45° in the clockwise direction to cause the fluid to cover viewing port 42 as depicted in FIG. 4 where spectrophotometric readings are taken from which the change in turbidity as a function of time is determined. By comparing these readings with graphs prepared using a urine sample containing known amounts of protein, the protein concentration in the test sample is determined.

Figure 5:
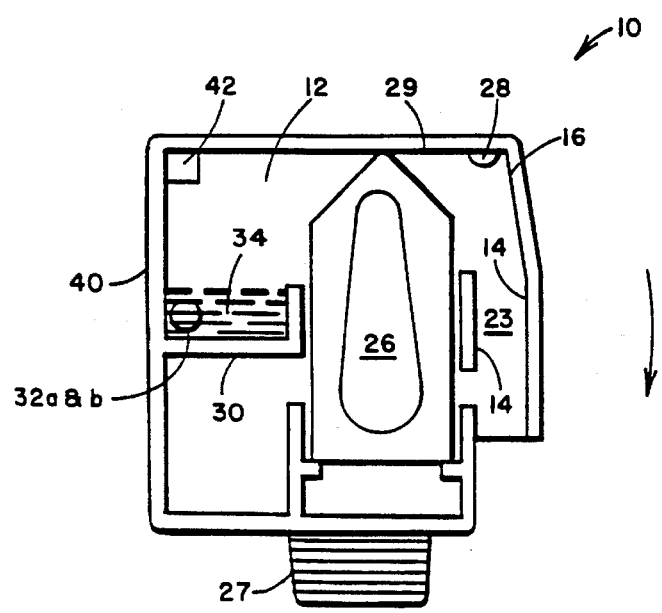

The system is now ready for the second step of the analytical procedure which is the determination of creatine concentration. A suitable creatinine reagent such as LiD-NBA is dried onto the second reagent site 32a located in the second reaction zone 34. The alkaline reagent is dried onto the third reagent site 32b which is on the opposite wall of the vessel from reagent site 32a so that they are physically separated from each other. After the protein assay is completed, the vessel is rotated another 135° to the right to invert it from its original position and bring the buffer solution into contact with the dried creatinine detecting reagent at reagent site 32a and the alkaline reagent at site 32b as depicted in FIG. 5 thereby causing their solubilization. This results in an increase in the buffer solution's pH to the level of from about 11.5 to 12.5 necessary for the creatinine determination reaction to take place. The color change resulting from the interaction of the creatinine reagent and creatinine in the urine is determined spectrophotometrically. This can be done by rotating the reaction vessel 135° in the counter clockwise direction and taking a reading through viewing port 42. The results of this reading are compared with readings taken on urine samples containing known concentrations of creatinine.

The use of the lithium salt of the creatinine detecting reagent will increase the solubilization rate of the creatinine detecting reagent and also permit the formation of more concentrated solutions of this reagent. The dried creatinine detecting reagent and alkaline material used in the second reaction zone of the above described device are prepared as follows:

A. Preparation of Dried Li-DNBA Reagent

Dinitrobenzoic acid (DNBA, 3.4 g) was mixed with lithium hydroxide (2.5M solution, 6.2 ml). All of the DNBA was dissolved to give a light yellowish solution having a pH of about 4.7. The solution was diluted with 0.54 ml of distilled water and 4.5 ml of the mixture was mixed with 0.5 gm of sucrose to make a 10% sucrose solution. A portion of this mixture (15 µl) was deposited into site 32a of the second reaction zone of the reagent cartridge and dried using a drying tunnel operated at 60° C. and a drying time of 15 minutes.

B. Preparation of Dried Alkaline Reagent

Potassium phosphate, dibasic, trihydrate (22.8 g) was mixed with potassium hydroxide (2.5M) and the total volume was brought up to 100 ml with the potassium hydroxide. A 4.5 ml aliquot of the mixture was mixed with 0.5 g of sucrose to make a 10% sucrose solution. This mixture (15 µL) was deposited onto site 32b of the second reaction zone of the reagent cartridge and dried using a drying tunnel operated at 60° C. and a drying time of 15 minutes.

What is claimed is:

1. An assay for a urinary protein and creatinine which comprises the steps of:
   a) providing a reaction vessel having a substantially horizontal axis of rotation and an analytical reaction channel containing first and second reaction zones, the second reaction zone situated a predetermined distance from and in fluid communication with the first reaction zone whereby a liquid test sample disposed in the reaction channel is capable of being transported by gravity along the reaction channel between the reaction zones by rotating the reaction vessel along its axis of rotation; delivery means for providing a unidirectional flow of a liquid test sample into the reaction vessel and inlet means in liquid communication with the delivery means for introducing the liquid test sample into the delivery means, the first reaction zone having an antibody reagent dried therein and the second reaction zone containing a dried lithium salt of an organic acid capable of reacting with creatinine under alkaline conditions in which the pH is from about 11.5 to 12.5 to form a colored reaction product therewith and a dried alkaline material which upon rehydration is capable of providing the necessary alkalinity for the creatine/organic acid reaction, said reaction vessel also having a viewing port between the first and second reaction zones;
   b) introducing urine suspected of containing protein and creatinine as the liquid test sample into the reaction vessel through the delivery means and also introducing a reaction fluid containing a polymeric agglutinator which specifically binds with the antibody reagent dried in the first reaction zone to thereby solubilize the antibody reagent and cause an agglutination reaction which is quantified by the taking of readings through the viewing port;
   c) rotating the reaction vessel about its axis of rotation to bring the liquid test sample/reaction fluid combination into contact with the lithium salt of the organic acid and alkaline material thereby causing their dissolution and raising the pH to a level of from about 11.5 to 12.5 and resulting in a colored response between the organic acid anion and any creatinine present in the liquid test sample and determining the magnitude of this colored response as a function of the creatinine in the urine sample.

2. The assay of claim 1 wherein the organic acid is 3,5-dinitrobenzoic acid, picric acid or 1,4-napthoquinone-2-sulfonic acid.

3. The assay of claim 2 wherein the organic acid is 3,5-dinitrobenzoic acid.

4. The assay of claim 1 wherein the alkaline material is an alkali metal hydroxide.

5. The assay of claim 4 wherein the alkali metal hydroxide is potassium, sodium or lithium hydroxide.

6. The assay of claim 1 wherein the magnitude of the colored response is determined by taking a spectrophotometric reading through the viewing port and comparing the results of this reading with readings taken on urine samples containing known concentrations of creatinine.

\* \* \* \* \*